(12) United States Patent
Pifferi

(10) Patent No.: US 7,250,428 B2
(45) Date of Patent: Jul. 31, 2007

(54) CETYLPYRIDINIUM SALT OF AN ANTI-INFLAMMATORY AGENT AND PHARMACEUTICAL COMPOSITIONS CONTAINING IT

(75) Inventor: Giorgio Pifferi, Milan (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 177 days.

(21) Appl. No.: 10/544,224

(22) PCT Filed: Feb. 12, 2004

(86) PCT No.: PCT/EP2004/001412

§ 371 (c)(1),
(2), (4) Date: Aug. 2, 2005

(87) PCT Pub. No.: WO2004/072017

PCT Pub. Date: Aug. 26, 2004

(65) Prior Publication Data

US 2006/0142353 A1 Jun. 29, 2006

(30) Foreign Application Priority Data

Feb. 14, 2003 (IT) .................. MI2003A0269

(51) Int. Cl.
*A01N 43/40* (2006.01)
(52) U.S. Cl. ................... 514/358; 546/347
(58) Field of Classification Search ............ 546/347; 514/358
See application file for complete search history.

(56) References Cited

U.S. PATENT DOCUMENTS

| 4,407,824 A | 10/1983 | Eckert |
| 5,614,223 A | 3/1997 | Sipos |

FOREIGN PATENT DOCUMENTS

| DE | 198 56 101 | 6/2000 |
| EP | 0 271 709 | 6/1988 |
| EP | 0521393 A2 * | 6/1992 |
| EP | 0 521 393 | 1/1993 |
| JP | 2000 256186 | 9/2000 |

* cited by examiner

*Primary Examiner*—Thomas McKenzie
*Assistant Examiner*—Binta Robinson
(74) *Attorney, Agent, or Firm*—Oblon, Spivak, McClelland, Maier & Neustadt, P.C.

(57) ABSTRACT

Cetylpyridinium salt of diclofenac.

11 Claims, No Drawings

CETYLPYRIDINIUM SALT OF AN ANTI-INFLAMMATORY AGENT AND PHARMACEUTICAL COMPOSITIONS CONTAINING IT

The present invention relates to a cetylpyridinium salt of an anti-inflammatory agent and to pharmaceutical compositions containing it.

It is known that many arylacetic and arylpropionic acids and basic addition salts thereof, with pharmaceutically acceptable organic and mineral bases, have wide application as non-steroidal anti-inflammatory drugs (NSAIDs), both systemically and topically.

The efficacy of NSAIDs is widely documented. However, it is also known that their therapeutically useful activity is accompanied by adverse side effects, particularly on the gastric mucosa, above all when they are administered systemically. Thus, in the case of localized pathologies, they are preferably administered topically.

To this end, since the acid form of NSAIDs is virtually insoluble in water, numerous basic addition salts with pharmaceutically acceptable organic and mineral bases have been investigated.

Some NSAIDs form, relatively easily, basic addition salts having a solubility in water that is suitable for them to be incorporated in pharmaceutical forms for topical use, for instance gels, creams, pomades, eyedrops, mouthwashes, vaginal rinses and the like.

On the other hand, for other NSAIDs, the solubility in water of the basic addition salts is insufficient to prepare pharmaceutical forms for topical use without resorting to the use of solubilizing agents such as alcohols, surfactants and the like.

One of these NSAIDs is diclofenac (2-(2,6-dichloroanilino)phenylacetic acid). As is known in the literature, the only diclofenac salt endowed with sufficient water solubility to prepare pharmaceutical forms for topical use is the choline salt (EP-A-0 521 393). However, this salt has the typical drawbacks of choline, characterized by an unpleasant odour and taste. These organoleptic properties are thus particularly negative in the case of pharmaceutical forms for the topical treatment of diseases of the oropharyngeal cavity, such as mouthwashes and sprays, the therapeutic activity of which is proportionately greater the longer they rest in contact with the mucosae.

It is also known that localized inflammations are frequently sustained or accompanied by bacterial infections or are consequent to surgical operations. In both cases, along with the anti-inflammatory treatment, it is necessary to administer and antibacterial agent for therapeutic or prophylactic purposes.

To this end, a pharmaceutical form for topical use containing a combination of two different compounds: a basic addition salt of an NSAID, which is sufficiently water-soluble, and an antibacterial agent that is also sufficiently water-soluble, should be prepared. However, it is no trivial matter to find two compounds which, in addition to having the abovementioned physicochemical properties, also have optimum activity spectra, are mutually compatible and give pharmaceutical forms that are stable over time.

It has now been found that the cetylpyridinium (1-hexadecylpyridinium) salt of diclofenac has these characteristics.

Even more surprisingly, it has been found that this salt is not sufficiently soluble in water but that, in the presence of water, it swells to give solutions/suspensions of gelatinous consistency that tend to incorporate appreciable amounts of air. This property is particularly advantageous in the preparation of pharmaceutical forms for topical use, since it is not necessary to add viscosifying excipients.

In addition, this salt is relatively palatable.

This salt is a stable crystalline solid with a sharp melting point (52-55° C.).

Its stability in the presence of water is virtually infinite and, consequently, sufficient for pharmaceutical use.

In one aspect, the present invention thus relates to the cetylpyridinium salt of diclofenac, of formula (I)

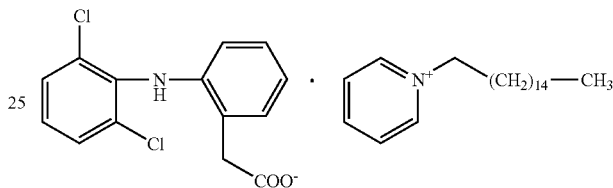

(I)

In another aspect, the present invention relates, rather, to a method that comprises the preparation of the cetylpyridinium salt of diclofenac (I) according to the following scheme:

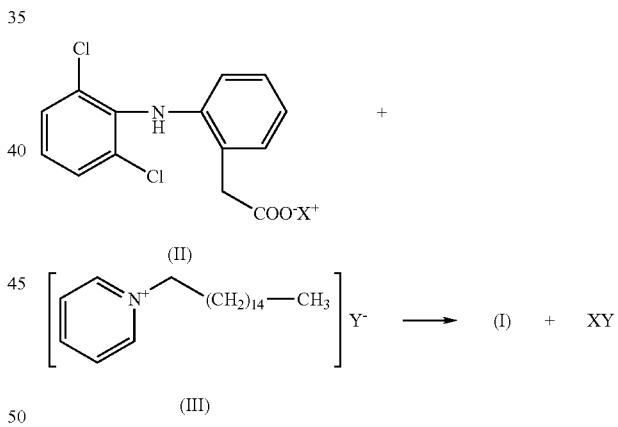

in which
X is H or a mineral or organic cation, and
Y is OH or halogen,
in a suitable solvent, and separation of the salt (I) thus obtained via conventional techniques.

Examples of preferred cations are the alkali metals.

In a first preferred embodiment, the sodium salt of diclofenac is reacted with cetylpyridinium chloride.

In a second preferred embodiment, diclofenac acid (X=H) is reacted with cetylpyridinium hydroxide.

The preferred solvent is water. Examples of other suitable solvents are aliphatic hydrocarbons, aromatic hydrocarbons, ketones and low molecular weight halohydrocarbons.

Preferably, the low molecular weight aliphatic halohydrocarbon contains from 1 to 3 carbon atoms. Even more preferably, it is selected from the group comprising methylene-chloride, chloroform, carbon tetrachloride, dichloroethane, trichloroethane, tetrachloroethane, trichloroethylene and trichloropropane.

The salt (I) of the invention thus formed is isolated via conventional techniques such as phase separation or evaporation of the solvent.

In a further aspect, the present invention relates to a pharmaceutical composition containing an effective dose of the cetylpyridinium salt of diclofenac (I) and at least one pharmaceutically acceptable inert ingredient.

Preferably, the pharmaceutically acceptable compositions of the present invention are prepared in the form of suitable dosage forms.

Examples of suitable dosage forms are tablets, capsules, coated tablets, granules, solutions and syrups for oral administration; creams, gels, ointments, pomades, medicated toothpastes, medicated plasters, eyedrops, mouthwashes and vaginal rinses for topical administration; suppositories for rectal administration, sterile solutions for administration by injection, and aerosols.

The dosage forms for topical administration are preferred.

The dosage forms may also contain other conventional ingredients that are well known in the art, for instance: preserving agents, stabilizers, buffers, salts for regulating the osmotic pressure, sweeteners, emulsifiers, colorants, flavourings and the like.

Pharmaceutical forms in the form of solutions or suspensions of gelatinous consistency are particularly preferred. These may be readily prepared by simple addition of water. Typically, the weight ratio between the salt of the present invention and water ranges from 1:1 to 1:15. Advantageously, preserving agents and flavourings may also be added. One characteristic of the suspensions of gelatinous consistency according to the present invention is that it is not necessary to add viscosifying polymers, such as polysiloxanes, poloxamers, carboxymethylcellulose, carboxyvinyl polymers and the like, which are commonly necessary in order to obtain a gel.

If required by particular therapies, the pharmaceutical composition of the present invention may contain other pharmacologically active ingredients whose simultaneous administration is useful.

In the pharmaceutical composition of the present invention, the dose of the cetylpyridinium salt of diclofenac (I) may vary within a wide range depending on known factors, for instance the type of disease to be treated, the severity of the disease, the patient's body weight, the dosage form, the prescribed route of administration and the number of daily administrations.

However, the optimum amount may be determined by a person skilled in the art easily and routinely on the basis of the known activities of diclofenac and of cetylpyridinium as a function of the therapy.

The dosage forms of the pharmaceutical composition of the present invention may be prepared according to techniques that are well known to pharmaceutical chemists, which include mixing, granulation, compression, dissolution, sterilization and the like.

Advantageously, the pharmaceutical composition of the present invention may be used in traumatology, phlebology, odontostomatology, laryngology, otology, rhinology, ophthalmology, urology, gynaecology, proctology, dermatology and the like.

The examples that follow serve to illustrate the invention without, however, limiting it.

EXAMPLE 1

Preparation of the Cetylpyridinium Salt of Diclofenac (Method A)

A solution, preheated to 60° C., of cetylpyridinium chloride monohydrate (5.35 g; 14.94 mmol) in water (60 mL) was rapidly added dropwise to a solution of sodium diclofenac (5.0 g; 15.72 mmol) in water (50 mL), with stirring at 60° C.

After stirring at 60° C. for 3 hours, the solution was cooled. Two phases formed. The lower oily phase was collected, while the aqueous phase was extracted with dichloromethane (70 mL).

The oily phase was taken up in dichloromethane (20 mL), resulting in the separation of an aqueous phase, which was discarded.

The two organic phases were combined, dried over anhydrous sodium sulphate and evaporated to dryness under vacuum. The oily residue (8.87 g) was solidified by trituration from cold isopropyl ether (25 mL) to give a crystalline white solid with a melting point of 52-55° C.

$H_2O$ (K.F.); 3.1%: $^1$H-NMR ($CDCl_3$) δ 0.88 (t, 3H, J=6.4 Hz), 1.10-1.40 (m, 26H), 1.79-1.97 (m, 2H), 3.05 (s, 2H, $H_2O$), 3.66 (s, 2H), 4.69 (t, 2H, J=7.2 Hz), 6.44 (d, 1H, J=7.4 Hz), 6.74-7.01 (m, 3H), 7.18 (d, 1H, J=6.2 Hz), 7.29 (d, 2H, J=9.0 Hz), 7.78-7.87 (m, 2H), 8.12-8.22 (m, 1H), 8.96 (d, 2H, J=5.6 Hz), 9.62 (bs, 1H).

EXAMPLE 2

Preparation of the Cetylpyridinium Salt of Diclofenac (Method B)

Sodium diclofenac (3.18 g; 10 mmol) and cetylpyridinium chloride (3.40 g; 10 mmol) were reacted together with stirring at room temperature in methylene chloride (40 mL) until the exchange reaction was substantially complete (about 30 minutes).

After removing the sodium chloride formed by filtration under reduced pressure, the organic solution was washed with water (5 mL). The water was separated from the emulsion and the organic phase was dried over anhydrous sodium sulphate.

The solvent was removed and the residue was taken up in isopropyl ether and left to stand overnight under cold conditions.

The solid product formed was collected by filtration and dried under reduced pressure.

A white solid was thus obtained (5.4 g); m.p. 52-55° C. with spectroscopic characteristics identical to those reported in Example 1.

EXAMPLE 3

Gel/Suspension for Topical Use

| | |
|---|---|
| Cetylpyridinium salt of diclofenac | 1.00 g |
| Purified water | 4.00 g |

EXAMPLE 4

Mouthwash

A solution having the composition below was prepared according to conventional techniques:

| | |
|---|---|
| Cetylpyridinium salt of diclofenac | 0.20 g |
| Xylitol | 10.0 g |
| Sodium benzoate | 1.00 g |
| Natural flavourings | 0.30 g |
| Colorant E114 | 0.20 g |
| Purified water qs | 100 g |

EXAMPLE 5

Medicated Toothpaste

A toothpaste having the composition below was prepared according to conventional techniques:

| | |
|---|---|
| Cetylpyridinium salt of diclofenac | 0.10 g |
| Xylitol | 5.00 g |
| Sodium monofluoroborate | 0.15 g |
| Natural flavourings | 0.45 g |
| Sodium lauryl sulphate | 0.10 g |
| Xanthan gum | 10.0 g |
| Colorant E131 | 0.20 g |
| Purified water qs | 100 g |

EXAMPLE 6

Gingival Gel

A gel having the composition below was prepared according to conventional techniques:

| | |
|---|---|
| Cetylpyridinium salt of diclofenac | 1.00 g |
| Kathon ™ | 0.65 g |
| Disodium EDTA | 0.10 g |
| Polyethoxylated hydrogenated castor oil | 6.00 g |
| Poloxamer ™ 407 | 22.0 g |
| Polysorbate | 6.00 g |
| Sodium chloride | 0.50 g |
| Sterile purified water qs | 100 g |

EXAMPLE 7

Proctological Pomade

A pomade having the composition below was prepared according to conventional techniques:

| | |
|---|---|
| Cetylpyridinium salt of diclofenac | 0.50 g |
| Benzocaine | 1.00 g |
| Liquid paraffin | 3.00 g |
| Polyethylene glycol (mixture) | 50.0 g |
| White petroleum jelly | 10.0 g |
| Propylene glycol | 10.0 g |
| Talc | 5.00 g |
| Sterile purified water qs | 100 g |

The invention claimed is:

1. Cetylpyridinium salt of diclofenac, of formula (I)

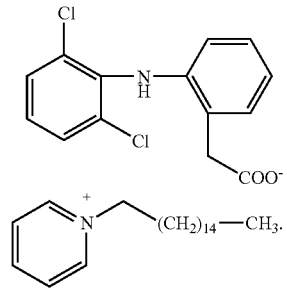

2. Cetylpyridinium salt of diclofenac (I) according to claim 1, characterized in that it melts at 52-55° C.

3. A method comprising the preparation of the cetylpyridinium salt of diclofenac (I) according to the following scheme:

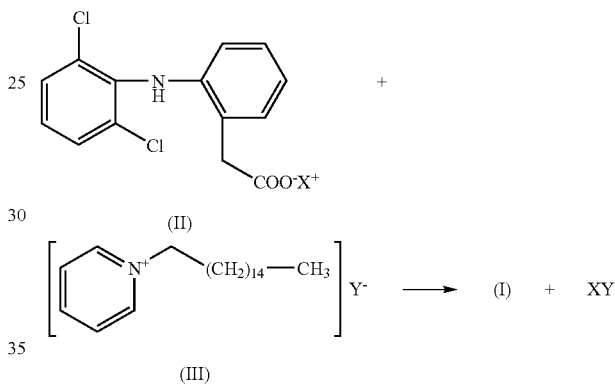

in which

X is H or a mineral or organic cation, and

Y is OH or halogen, in a suitable solvent, and separation of the salt (I) thus obtained via conventional techniques.

4. The method according to claim 3, characterized in that X is an alkali metal.

5. The method according to claim 3, characterized in that Y is Cl.

6. The method according to claim 3, characterized in that the solvent is water.

7. The method according to claim 3, characterized in that the solvent is a low molecular weight halohydrocarbon.

8. The method according to claim 7, characterized in that the halohydrocarbon contains from 1 to 3 carbon atoms.

9. The method according to claim 8, characterized in that the halohydrocarbon is selected from the group comprising methylene chloride, chloroform, carbon tetrachloride, dichloroethane, trichloroethane, tetrachloroethane, trichloroethylene and trichloropropane.

10. Pharmaceutical composition, characterized in that it contains an effective dose of cetylpyridinium salt of diclofenac (I) and at least one pharmaceutically acceptable inert ingredient.

11. Pharmaceutical composition according to claim 9, characterized in that the cetylpyridinium salt of diclofenac (I) melts at 52-55° C.

* * * * *